United States Patent
Mo

(10) Patent No.: US 10,730,165 B2
(45) Date of Patent: Aug. 4, 2020

(54) TWO-STAGE PINCER

(71) Applicant: Dechao Mo, Guangxi (CN)

(72) Inventor: Dechao Mo, Guangxi (CN)

(73) Assignee: Dechao Mo, Beiliu (CN)

( * ) Notice: Subject to any disclaimer, the term of this patent is extended or adjusted under 35 U.S.C. 154(b) by 320 days.

(21) Appl. No.: 15/995,759

(22) Filed: Jun. 1, 2018

(65) Prior Publication Data

US 2018/0272502 A1    Sep. 27, 2018

Related U.S. Application Data

(63) Continuation of application No. PCT/CN2016/000670, filed on Dec. 5, 2016.

(30) Foreign Application Priority Data

Mar. 2, 2016    (CN) .......................... 2016 1 0116194

(51) Int. Cl.
  *B25B 7/12*    (2006.01)
  *B25B 7/00*    (2006.01)
  *B25G 1/08*    (2006.01)

(52) U.S. Cl.
  CPC ................. *B25B 7/12* (2013.01); *B25B 7/00* (2013.01); *B25G 1/08* (2013.01)

(58) Field of Classification Search
  CPC .... B25B 7/06; B25B 7/08; B25B 7/10; B25B 7/12
  See application file for complete search history.

(56) References Cited

U.S. PATENT DOCUMENTS

| 3,169,307 | A | * | 2/1965 | Langwell | ................ B25B 7/16 |
|---|---|---|---|---|---|
| | | | | | 29/229 |
| 3,170,345 | A | * | 2/1965 | Poingt | ...................... B25B 7/18 |
| | | | | | 72/409.12 |
| 4,662,252 | A | * | 5/1987 | Warheit | .................... B25B 7/10 |
| | | | | | 81/341 |
| 5,469,765 | A | * | 11/1995 | Franklin | ................. B25B 5/127 |
| | | | | | 269/228 |
| 5,509,291 | A | * | 4/1996 | Nilsson | ............... H01R 43/042 |
| | | | | | 72/409.14 |

(Continued)

FOREIGN PATENT DOCUMENTS

| CN | 1270093 A | 10/2000 |
|---|---|---|
| CN | 2846024 Y | 12/2006 |

(Continued)

*Primary Examiner* — David B. Thomas
(74) *Attorney, Agent, or Firm* — Wayne & Ken, LLC; Tony Hom

(57) ABSTRACT

Two-stage pincers as hand-operated tools, especially multi-functional wrenches automatically switching between two stages and having a large-opening jaw and a high clamping force, comprising: a first main structure (1), a second main structure (2), a handle (3), a pawl (4), a first pin (5), a second pin (6), a first connecting rod (7), a second connecting rod (8), a first stop nut (9), a second stop nut (10), a first preloaded spring (11), a second preloaded spring (12), a supporting spring (13), a small pin (15), a second small pin (14), a third pin (18), a fourth pin (16) and a fifth pin (17). The two-stage pincers overcome problems of the existing hand-operated tools, i.e. wide varieties, inconvenience to carry and low efficiency.

5 Claims, 4 Drawing Sheets

(56) References Cited

U.S. PATENT DOCUMENTS

| | | | | |
|---|---|---|---|---|
| 5,970,827 | A * | 10/1999 | Lin | B25B 7/10 81/409 |
| 6,000,303 | A * | 12/1999 | Chang | B25B 7/10 81/341 |
| 6,014,917 | A * | 1/2000 | Bally | B25B 7/10 81/355 |
| 6,065,376 | A * | 5/2000 | Khachatoorian | B25B 7/10 81/341 |
| 6,467,380 | B1 * | 10/2002 | Azkona | B25B 7/10 81/357 |
| 6,658,971 | B2 * | 12/2003 | Delbrugge, Jr. | B25B 7/10 81/355 |
| 6,662,690 | B1 * | 12/2003 | Ploeger | B25B 7/12 81/318 |
| 7,117,771 | B2 * | 10/2006 | Whiteford | B25B 7/00 81/357 |
| 10,144,117 | B2 * | 12/2018 | Khristyuchenko | B25B 7/18 |
| 10,406,656 | B2 * | 9/2019 | Wang | B25B 7/10 |
| 2012/0216657 | A1 | 8/2012 | Marks | |

FOREIGN PATENT DOCUMENTS

| | | |
|---|---|---|
| CN | 203853900 U | 10/2014 |
| CN | 105269478 A | 1/2016 |

\* cited by examiner

TWO-STAGE PINCER

TECHNICAL FIELD

The present invention relates to hand-operated tool pincers, especially multifunctional wrenches automatically switching between two stages and having a large-opening jaw and a high clamping force. For convenience, they are called two-stage pincers for short.

BACKGROUND OF THE PRESENT INVENTION

In people's daily life and work, a wide variety of hand-operated tools are needed. Most of the existing hand-operated tools have a single function or general performance. For example, pliers have a small opening and a low clamping force, and their range of use is limited. Also for example, adjustable turbine wrenches are just used to screw nuts, and cannot be used as pincers. Some so-called multi-functional tools are just a simple combination of single-functional tools and their effects of use are not very ideal.

In short, the existing hand-operated tools, especially small-volume pincers for daily use which are manipulated by a single hand, have a single function and general performance, and need to be improved.

SUMMARY OF THE PRESENT INVENTION

The purpose of the present invention is to provide multifunctional hand-operated tool pincers having some prominent advantages, to overcome problems of the existing hand-operated tools, i.e. wide varieties, inconvenience to carry and low efficiency. For this purpose, the present invention employs the following technical solutions.

1. Two-stage pincers comprise a main structure (1), a main structure (2) and a handle (3), wherein
an upper portion of the main structure (1) is a multifunctional jaw; a pin (5) and a pin (6) are provided in a middle portion of the main structure (1), radial through holes in which connecting rods (7) and (8) can move are formed in axial middle portions of the pins (5, 6), and the pins (5, 6) can rotate but cannot move axially; a lower portion of the main structure (1) is connected to a spring (13), and the other end of the spring (13) is connected to the main structure (2); and a hole is formed in the lower portion of the main structure (1), a pin (18) is provided in the hole, and the pin (18) is hinged to the two main structures (1, 2).

2. An upper portion of the main structure (2) is a multifunctional jaw; a ratchet is provided on a lower end surface of a protrusion in a middle portion of the main structure (2), and a center of a base circle of the ratchet serves as a center of the pin (18); and a lower portion of the main structure (2) is a grip which can be of a hollow structure having a cavity in which practical small components can be put.

3. The handle (3) is hinged to the main structure (1) by a pin (16) at an upper portion, hinged to a pawl (4) by a pin (17) at a nearby position, and connected to the connecting rod (8) by a small pin (15) at a lower portion; and the handle (3) can be of a hollow structure having a cavity in which practical small components can be put if necessary.

4. The pawl (4) is connected to the connecting rod (7) by a small pin (14), the connecting rod (7) supports a preloaded spring (11), the other end of the spring (11) presses the pin (5), and there is a stop nut (9) at an end of the connecting rod (7).

5. The connecting rod (8) supports a preloaded spring (12), the other end of the spring (12) presses the pin (6), and there is a stop nut (10) at an end of the connecting rod (8).

BRIEF DESCRIPTION OF THE DRAWINGS

The present invention can be completely understood by the detailed description below and in combination with the drawings. The drawings do not form any limitations to the present invention and are merely used for facilitating the explanation and the understanding.

DETAILED DESCRIPTION OF THE PRESENT INVENTION

Figure 1:
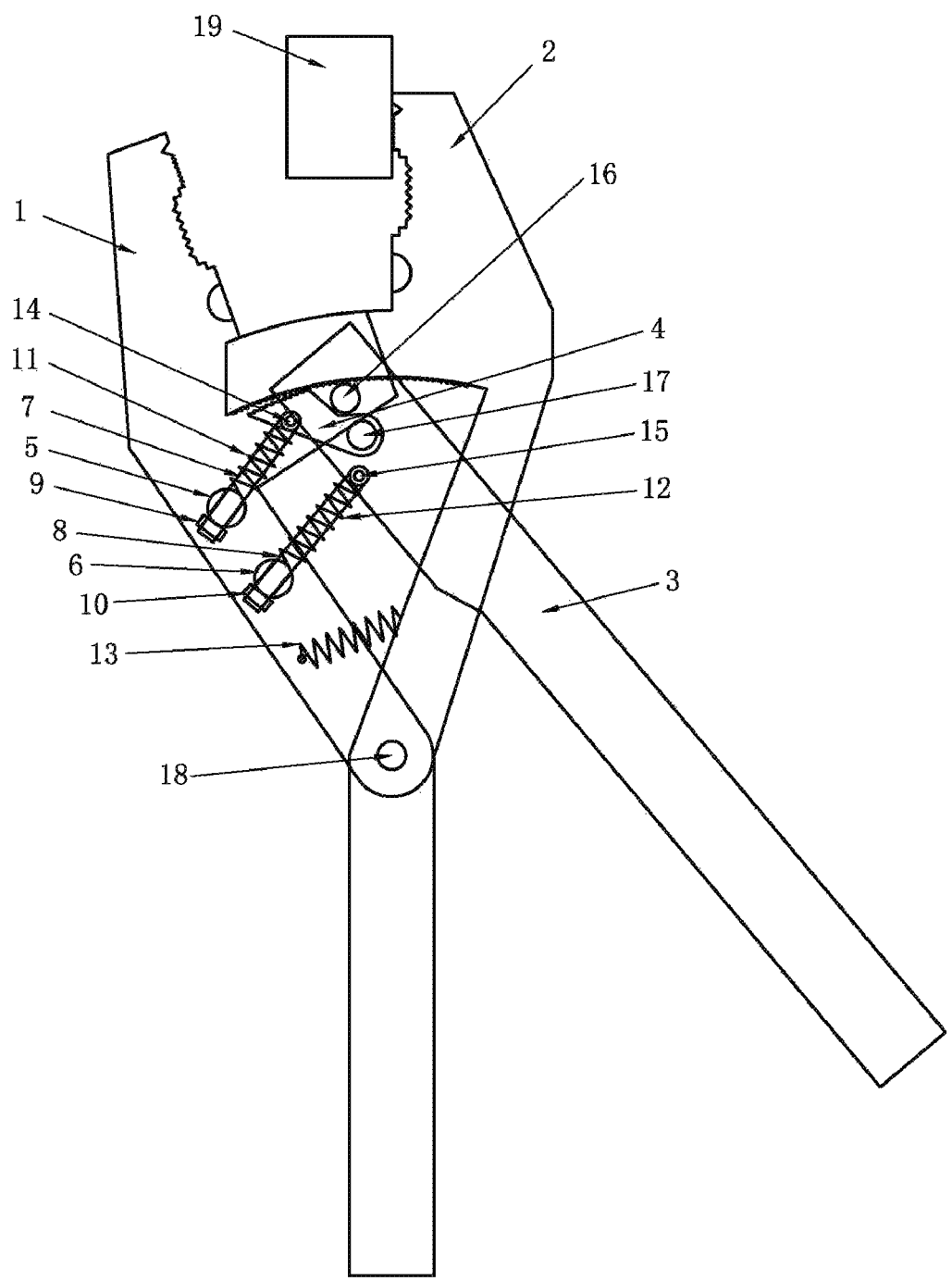
FIG. 1 is a schematic view showing the state of the two-stage pincers in a first stage according to the present invention.
Figure 2:
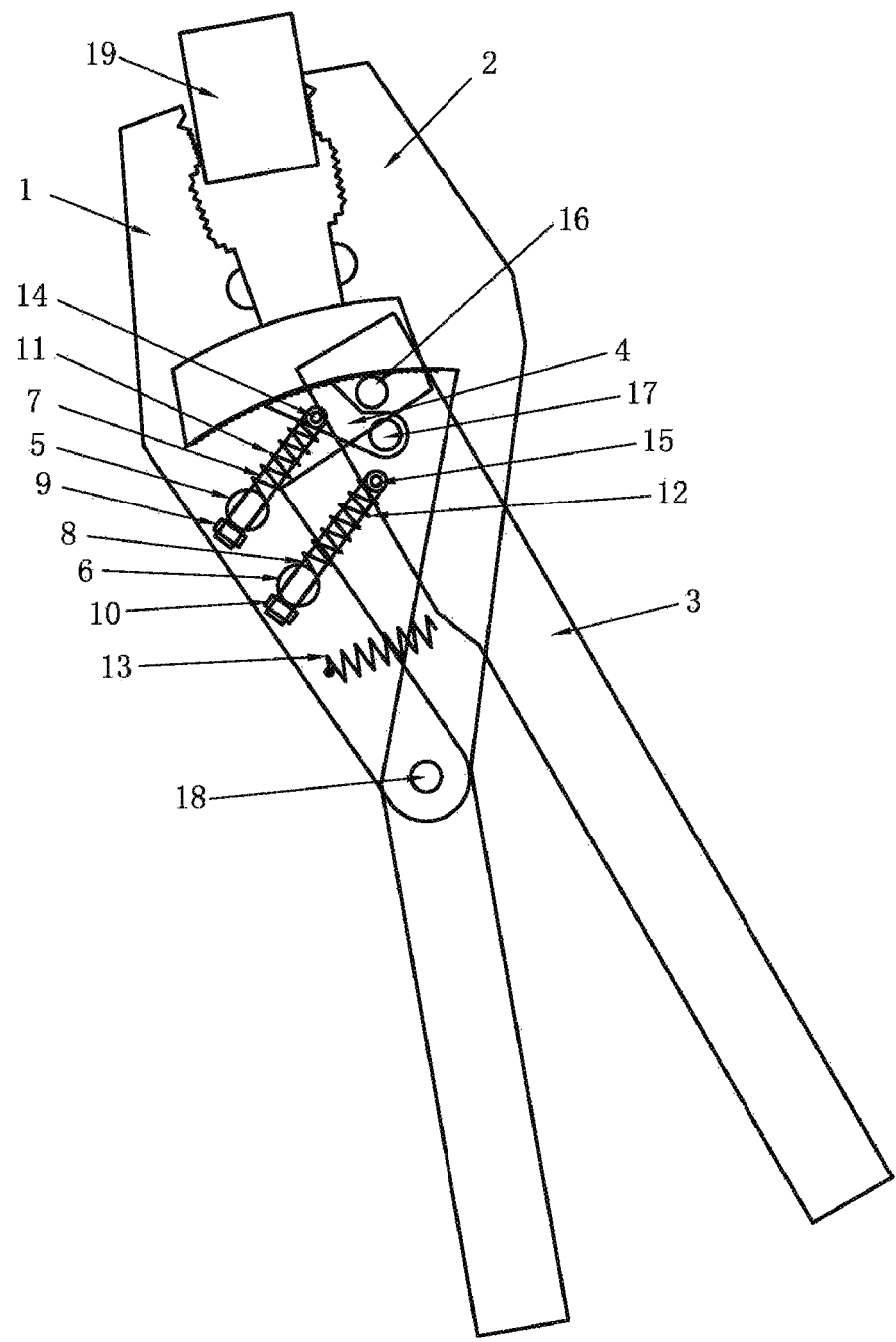
FIG. 2 is a schematic view showing the state of the two-stage pincers in a second stage.
Figure 3:
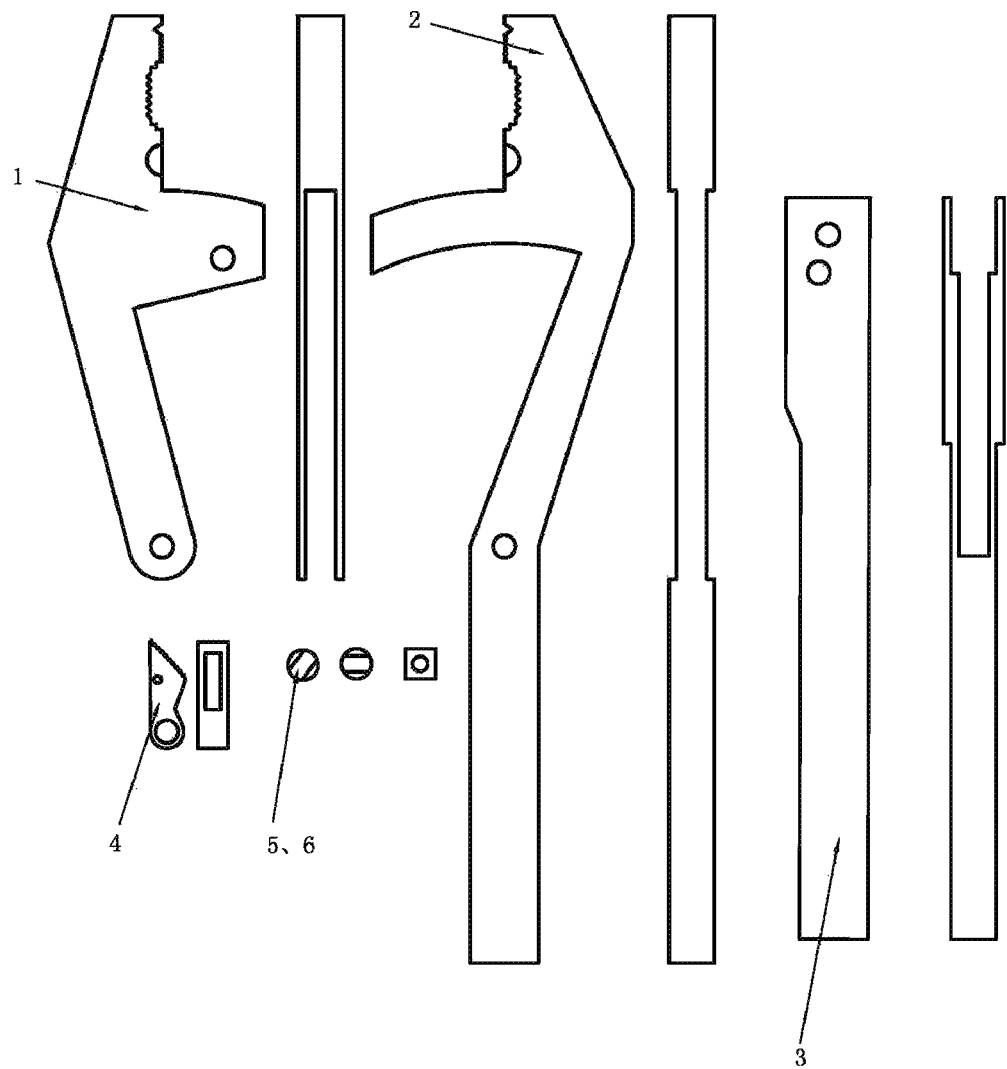
FIG. 3 is a front view and a side view of main components (1, 2, 3, 4, 5, 6), where the front view and the side view of components are arranged side by side, and the figure of components (5, 6) represents that pins (5, 6) can be rotated and middle through holes can be seen from the side of the pins.
Figure 4:
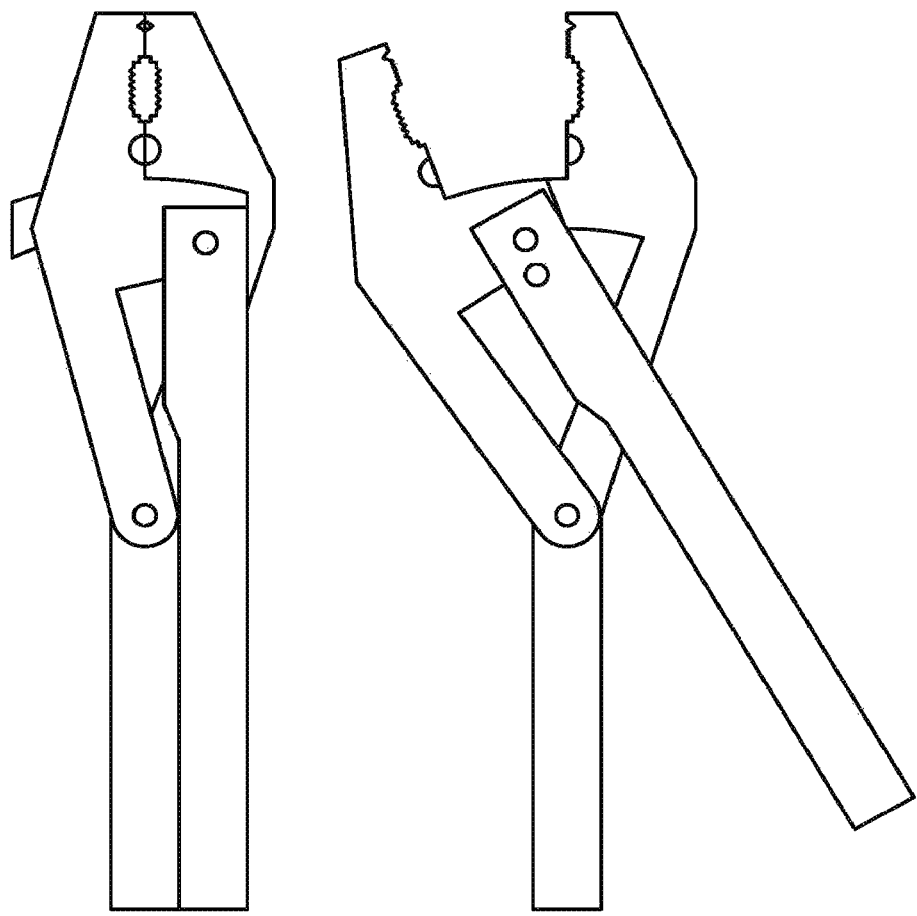
FIG. 4 is a rough schematic view showing the appearance of the pincers in a closed state and an open state, where only three main components are shown in the figure.

The present invention will be further described below with reference to the drawings of the specification.

1. Two-stage pincers comprise a main structure (1), a main structure (2) and a handle (3), wherein
an upper portion of the main structure (1) is a multifunctional jaw; a pin (5) and a pin (6) are provided in a middle portion of the main structure (1), radial through holes in which connecting rods (7) and (8) can move are formed in axial middle portions of the pins (5, 6), and the pins (5, 6) can rotate but cannot move axially; a lower portion of the main structure (1) is connected to a spring (13), and the other end of the spring (13) is connected to the main structure (2); and a hole is formed in the lower portion of the main structure (1), a pin (18) is provided in the hole, and the pin (18) is hinged to the two main structures (1, 2).

2. An upper portion of the main structure (2) is a multifunctional jaw; a ratchet is provided on a lower end surface of a protrusion in a middle portion of the main structure (2), and a center of a base circle of the ratchet serves as a center of the pin (18); and a lower portion of the main structure (2) is a grip which can be of a hollow structure having a cavity in which practical small components can be put.

3. The handle (3) is hinged to the main structure (1) by a pin (16) at an upper portion, hinged to a pawl (4) by a pin (17) at a nearby position, and connected to the connecting rod (8) by a small pin (15) at a lower portion; and the handle (3) can be of a hollow structure having a cavity in which practical small components can be put if necessary.

4. The pawl (4) is connected to the connecting rod (7) by a small pin (14), the connecting rod (7) supports a preloaded spring (11), the other end of the spring (11) presses the pin (5), and there is a stop nut (9) at an end of the connecting rod (7).

5. The connecting rod (8) supports a preloaded spring (12), the other end of the spring (12) presses the pin (6), and there is a stop nut (10) at an end of the connecting rod (8).

When the pincers are used to clamp or cut a workpiece, grips (2, 3) are first driven so that the jaw is opened to a size greater than the corresponding size of the workpiece in order to put the workpiece into the jaw. The preloaded spring (13) is helpful to open the jaw.

After the workpiece is put into the jaw, the grips (2, 3) are driven to close the jaw. The main structure (1) and the handle (3) are connected by the pin (16) at a position and connected by the small pin (15), the connecting rod (8), the preloaded spring (12) and the pin (6) at another position, so that the main structure (1) and the handle (3) form a linkage body. During the movement, the handle (3) drives the main structure (1) to move by the elasticity of the preloaded spring (12), and then the jaw is closed and comes into contact with the workpiece (19). Before the jaw comes into contact with the workpiece, the driving force required for closing the jaw is small. In this case, the preloaded spring (12) provides enough preload force and the spring (12) is not further compressed. There is no relative movement between the main structure (1) and the handle (3), and jaw closing is realized only by the elasticity. This stage is one of origins of the name of the present invention, which is called a first stage. Since the ratio of the length of the main structure (1) to the length of the handle portion of the main structure (2) can be greater than 1, it can be known from the figure that the jaw can be quickly closed in the first stage. When the jaw is closed and comes into contact with the workpiece, the workpiece prevents the jaw from continuously closing. In this case, the operator continues closing the main structure (2) and the handle (3), so that the handle (3) rotates around the pin (16) which is regarded as a fulcrum and the pawl (4) is driven to engage with the main structure (2) in coordination with the preloaded spring (11). After the engagement is completed, the continuous movement of the handle (3) drives the pawl (4) and then drives the main structure (2) and the main structure (1) to move relative to each other, to close the jaw and clamp the workpiece (19) tightly. This stage is one of the origins of the name of the present invention, which is called a second stage. Since the distance between the pins (16, 17) is small, it can be known from the figure that the linear velocity of the pawl and the jaw during movement is low relative to the linear velocity of the lower portion of the handle (3). In other words, the jaw provides for a high clamping force.

In the second stage of the pincers, the stroke of the jaw is short. When it is required to clamp a soft workpiece or cut a thick linear object, if the jaw doesn't reach the required stroke when the grip is closed to its limit, two pincer heads can be held by a hand to prevent the jaw from opening, and then the grip is loosened. After the grip opens, the action of closing the grip is repeated. The above operation is repeated until the jaw reaches the required stroke.

After the clamping or cutting is finished, the grip is loosened and main moving components of the pincers perform inverse movement, i.e., go through the second stage first and then the first stage. The inverse movement process will not be repeated. The stop nuts (9, 10) can adjust the fit clearance to ensure the normal operation of the pincers and the manipulation performance thereof. In the first stage, the nut (9) is tangent to and resisted against the pin (5) so that the pawl will not come into contact with the main structure (2).

In the present invention, by the ingenious design in stages, the large opening and the high clamping force of the jaw can be ensured even in the case of single-hand manipulation. Therefore, the pincers can be used as wrenches, or be used as locking pincers, pliers, nutcrackers, pipe wrenches, water pump pincers, nail extractors or the like. When the pincers are used as adjustable wrenches, the wrenches can be quickly fitted with the nut without adjusting the worm gear, with high efficiency. When the nut is screwed, the rhythm of opening and closing is controlled by light training, so that the pincers have functions of ratchet wrenches. When a nut which is not fastened very tight is screwed, the jaw can clamp the nut tightly at almost all positions without considering the angle of the nut's edge. In this way, the pincers can be used in some spaces where rotation is limited and the operation efficiency is improved.

The pincers of the present invention may also be in other structures which will not affect the implementation of fundamental concepts of the present invention.

What is claimed is:

1. A two-stage pincer, comprising a main structure (1), a main structure (2) and a handle (3), wherein an upper portion of the main structure (1) is a multifunctional jaw; a pin (5) and a pin (6) are provided in a middle portion of the main structure (1), radial through holes in which connecting rods (7) and (8) can move are formed in axial middle portions of the pins (5, 6), and the pins (5, 6) can rotate but cannot move axially; a lower portion of the main structure (1) is connected to a spring (13), and the other end of the spring (13) is connected to the main structure (2); and a hole is formed in the lower portion of the main structure (1), a pin (18) is provided in the hole, and the pin (18) is hinged to the two main structures (1, 2).

2. The two-stage pincer according to claim 1, wherein an upper portion of the main structure (2) is a multifunctional jaw; a ratchet is provided on a lower end surface of a protrusion in a middle portion of the main structure (2), and a center of a base circle of the ratchet serves as a center of the pin (18); and a lower portion of the main structure (2) is a grip which can be of a hollow structure having a cavity in which practical small components can be put.

3. The two-stage pincer according to claim 1, wherein the handle (3) is hinged to the main structure (1) by a pin (16) at an upper portion, hinged to a pawl (4) by a pin (17) at a nearby position, and connected to the connecting rod (8) by a small pin (15) at a lower portion; and the handle (3) can be of a hollow structure having a cavity in which practical small components can be put if necessary.

4. The two-stage pincer according to claim 1, wherein the pawl (4) is connected to the connecting rod (7) by a small pin (14), the connecting rod (7) supports a preloaded spring (11), the other end of the spring (11) presses the pin (5), and there is a stop nut (9) at an end of the connecting rod (7).

5. The two-stage pincer according to claim 1, wherein the connecting rod (8) supports a preloaded spring (12), the other end of the spring (12) presses the pin (6), and there is a stop nut (10) at an end of the connecting rod (8).

* * * * *